United States Patent [19]

Shiber

[11] Patent Number: 5,443,443
[45] Date of Patent: * Aug. 22, 1995

[54] ATHERECTOMY SYSTEM

[75] Inventor: Samuel Shiber, Atkinson, N.H.

[73] Assignee: Surgical Systems & Instruments, Inc., Libertyville, Ill.

[*] Notice: The portion of the term of this patent subsequent to Mar. 22, 2005 has been disclaimed.

[21] Appl. No.: 107,453

[22] Filed: Aug. 17, 1993

Related U.S. Application Data

[63] Continuation-in-part of Ser. No. 913,231, Jul. 14, 1992, Pat. No. 5,334,211, which is a continuation-in-part of Ser. No. 662,558, Feb. 28, 1991, Pat. No. 5,306,244, which is a continuation-in-part of Ser. No. 499,726, Mar. 27, 1990, Pat. No. 5,135,531, which is a continuation-in-part of Ser. No. 350,020, May 12, 1989, Pat. No. 4,979,939, which is a continuation-in-part of Ser. No. 326,967, Mar. 22, 1989, Pat. No. 4,957,482, Ser. No. 324,616, Mar. 16, 1989, Pat. No. 5,007,896, Ser. No. 323,328, Mar. 13, 1989, Pat. No. 5,002,553, and Ser. No. 332,497, Mar. 13, 1989, Pat. No. 5,024,651, said Ser. No. 326,967, Ser. No. 324,616, Ser. No. 323,328, and Ser. No. 332,497, each is a continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 225,880, Jul. 29, 1988, Pat. No. 4,842,579, Ser. No. 205,479, Jun. 13, 1988, Pat. No. 4,883,458, and Ser. No. 78,042, Jul. 27, 1987, Pat. No. 4,819,634, said Ser. No. 225,880, Ser. No. 205,479, and Ser. No. 78,042, each is a continuation-in-part of Ser. No. 18,083, Feb. 24, 1987, Pat. No. 5,041,082, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.[6] ............................................. A61B 17/22
[52] U.S. Cl. ........................................ 604/22; 606/170
[58] Field of Search ................. 604/22; 606/159, 167, 606/169, 170, 171, 180; 128/751–755, 772

[56] References Cited

U.S. PATENT DOCUMENTS

| | | | |
|---|---|---|---|
| 2,505,358 | 4/1950 | Gusberg et al. | 128/751 |
| 3,433,226 | 3/1969 | Boyd | 606/159 |
| 3,614,953 | 10/1971 | Moss | 606/159 |
| 3,789,841 | 2/1974 | Antoshkiw | 128/772 |
| 4,030,503 | 6/1977 | Clark, III | 606/159 |
| 4,177,797 | 12/1979 | Baylis et al. | 128/754 |
| 4,249,541 | 10/1981 | Pratt | 128/753 |
| 4,445,509 | 5/1984 | Auth | 606/180 |
| 4,479,497 | 10/1984 | Fogarty et al. | 604/103 |
| 4,589,412 | 5/1986 | Kensey | 604/22 |
| 4,627,436 | 12/1986 | Leckrone | 606/159 |
| 4,669,469 | 6/1987 | Gifford, III et al. | 606/159 |
| 4,732,154 | 3/1988 | Shiber . | |
| 4,819,634 | 4/1989 | Shiber . | |
| 4,842,579 | 6/1989 | Shiber | 604/22 |
| 4,883,458 | 11/1989 | Shiber | 604/22 |
| 4,886,490 | 12/1989 | Shiber | 604/22 |
| 4,894,051 | 1/1990 | Shiber | 606/159 |
| 4,957,482 | 9/1990 | Shiber | 604/22 |
| 4,979,939 | 12/1990 | Shiber | 606/159 |
| 5,002,553 | 3/1991 | Shiber | 606/159 |
| 5,007,896 | 4/1991 | Shiber | 604/22 |
| 5,024,651 | 6/1991 | Shiber | 604/22 |
| 5,041,082 | 8/1991 | Shiber | 604/22 |
| 5,135,531 | 8/1992 | Shiber | 606/159 |

FOREIGN PATENT DOCUMENTS

| | | | |
|---|---|---|---|
| 2804015 | 8/1979 | Germany | 606/159 |
| 2044103 | 10/1980 | United Kingdom | 128/754 |
| 665908 | 6/1979 | U.S.S.R. | 606/159 |

Primary Examiner—Stephen C. Pellegrino
Assistant Examiner—Nancy Mulcare
Attorney, Agent, or Firm—Samuel Shiber

[57] ABSTRACT

A system for removing an obstruction, in sections, from within a vessel, having a flexible guide wire assembly which is insertable into the vessel and a flexible rotary catheter which is slidable over it, the flexible rotary catheter is equipped with a tubular blade at its distal end for cutting and separating the obstruction material from an inner wall of the vessel to be ingested by the system.

15 Claims, 6 Drawing Sheets

ATHERECTOMY SYSTEM

CROSS REFERENCE TO OTHER APPLICATIONS AND BACKGROUND OF THE INVENTION

This application is a continuation in part (CIP) of appl. Ser. No. 07/913,231 filed Jul. 14, 1992 (CT15 now U.S. Pat. No. 5,334,211) which is a CIP of appl. Ser. No. 07/662,558 filed Feb. 28, 1991 (CT14 now U.S. Pat. No. 5,306,244) which is a CIP of appl. Ser. No. 07/499,726 filed Mar. 27, 1990 (CT13 now U.S. Pat. No. 5,135,531) which is a CIP of appl. Ser. No. 07/350,020 filed May 12, 1989 (CT12 now U.S. Pat. No. 4,979,939) which is a CIP of four applications:

Appl. Ser. No. 07/326,967 filed Mar. 22, 1989 (CT11 now U.S. Pat. No. 4,957,482), appl. Ser. No. 07/324,616 filed Mar. 16, 1989 (CT10 now U.S. Pat. No. 5,007,896), appl. Ser. No. 07/323,328 filed Mar. 13, 1989 (CT9 now U.S. Pat. No. 5,002,553) and appl. Ser. No. 07/332,497 filed Mar. 13, 1989 (CT8 now U.S. Pat. No. 5,024,651).

These four applications are CIPs of appl. Ser. No. 07/286,509 filed Dec. 19, 1988 (CT7 now U.S. Pat. No. 4,894,051) which is a CIP of appl. Ser. No. 07/243,900 filed Sep. 13, 1988 (CT6 now U.S. Pat. No. 4,886,490), which is a CIP of three applications:

Appl. Ser. No. 07/225,880 filed Jul. 29, 1988 (CT5 now U.S. Pat. No. 4,842,579), appl. Ser. No. 07/205,479 filed Jun. 13, 1988 (CT4 now U.S. Pat. No. 4,883,458), and appl. Ser. No. 07/078,042 filed Jul. 27, 1987 (CT3 now U.S. Pat. No. 4,819,634).

These three applications are CIPs of appl. Ser. No. 07/018,083 filed Feb. 24, 1987 (CT2 now U.S. Pat. No. 5,041,082) which is a CIP of appl. Ser. No. 06/874,546 filed Jun. 16, 1986 (CT1 now U.S. Pat. No. 4,732,154) which is a CIP of appl. Ser. No. 06/609,846 filed May 14, 1984 (CT0 now abandoned).

All the above applications are being incorporated herein by reference.

BACKGROUND AND OBJECTIVES OF THE INVENTION

With age, a large percentage of the population develops atherosclerotic arterial obstructions resulting in diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide wire assembly, into the obstruction and then inflated to expand the obstruction's lumen (angioplasty). Some of the problems with angioplasty are injury to the arterial wall, creation of a rough lumen, and in a number of the cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy system having a flexible guide wire assembly which rotatably and slidably supports a flexible rotary catheter having a tubular blade at its distal end to cut and separate the obstruction from the artery and create a smooth lumen through it without cracking the arterial wall. The flexible guide wire assembly preferably defines voids for containing obstruction material.

Another objective is teach a design of an atherectomy catheter that lends itself to be produced in a range of diameters, down to about 1 mm (millimeter), and a length sufficient to reach remote arteries.

Another objective is teach a design of an atherectomy catheter that, in operation, would utilize existing skills of the medical staff such as gaining access to the patient vascular system and the manipulation of guide wires and catheters through it. These and other objectives of the invention will become apparent from the following discussion and the accompanying drawings.

BRIEF DESCRIPTION OF THE FIGURES

FIG. 5' shows an optional tubular blade design.

FIG. 7' shows an enlarged, partially sectioned view of the distal end section of a helical wire where the distal entry to the void, which is defined between the coils, is selectively closed by a thin walled cylinder.

DETAILED DESCRIPTION OF THE DRAWINGS

Figures 1, 3, 4, 5:
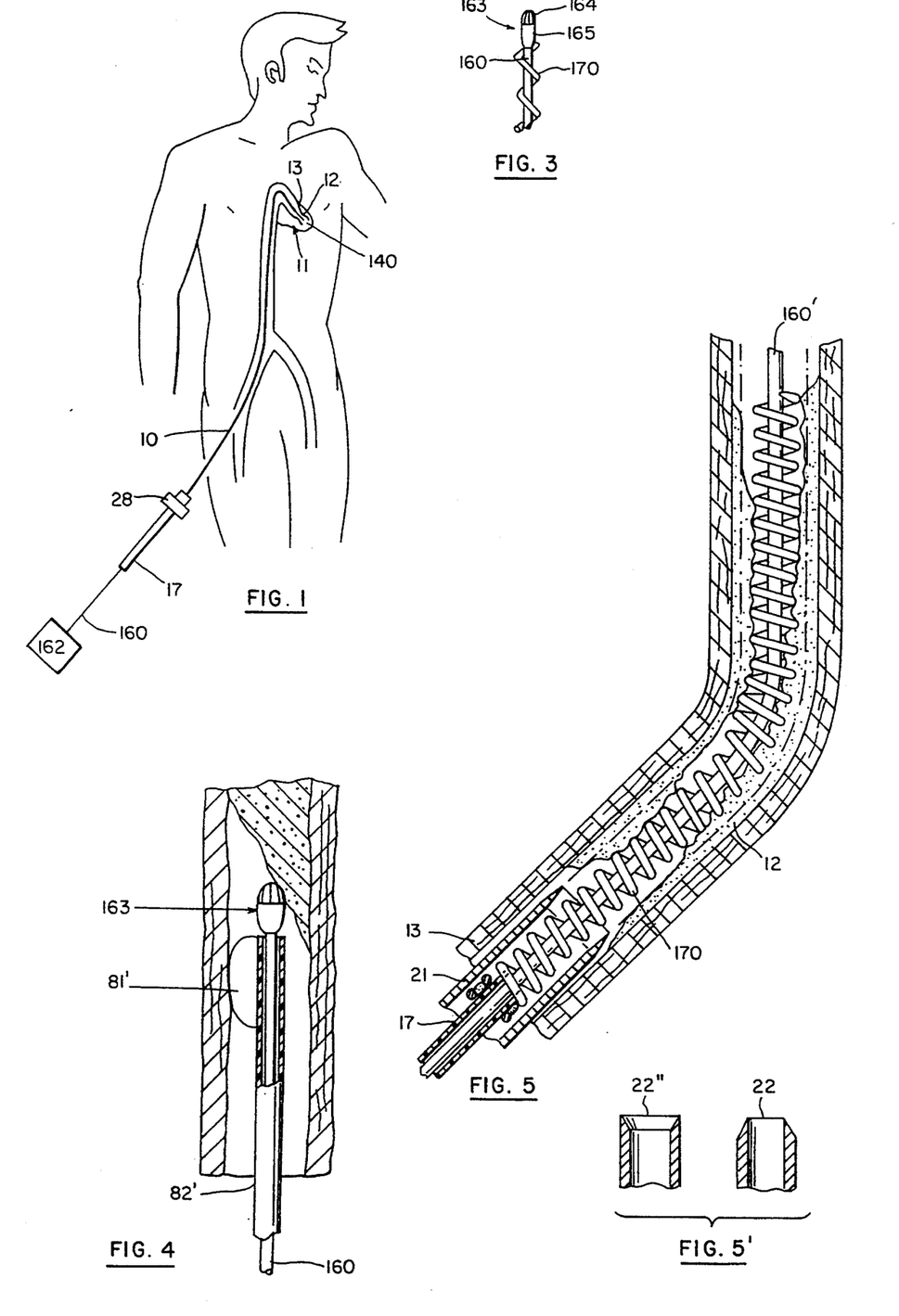
FIG. 1 generally shows an atherectomy system inserted at the groin area through the arterial system of a patient, into his obstructed coronary artery.
FIG. 3 shows an optional distal end of the ultrasound probe with teeth, or protrusions, on its distal end.
FIG. 4 shows a distal end of a flexible guide wire disposed in a deflecting catheter. The flexible guide wire has an ultrasound probe mounted at its distal tip. The transducer's distal end is equipped with teeth.
FIG. 5 shows the trajectory of the system in a cross sectioned, curved obstructed artery, when the atherectomy process is done over a flexible guide wire assembly over which the flexible rotary catheter is accurately guided.

FIG. 1 generally shows an atherectomy system 10 inserted at the groin area through the skin, through a patient's vascular system into a coronary artery 13 serving the patient's heart 11.

Figure 2:
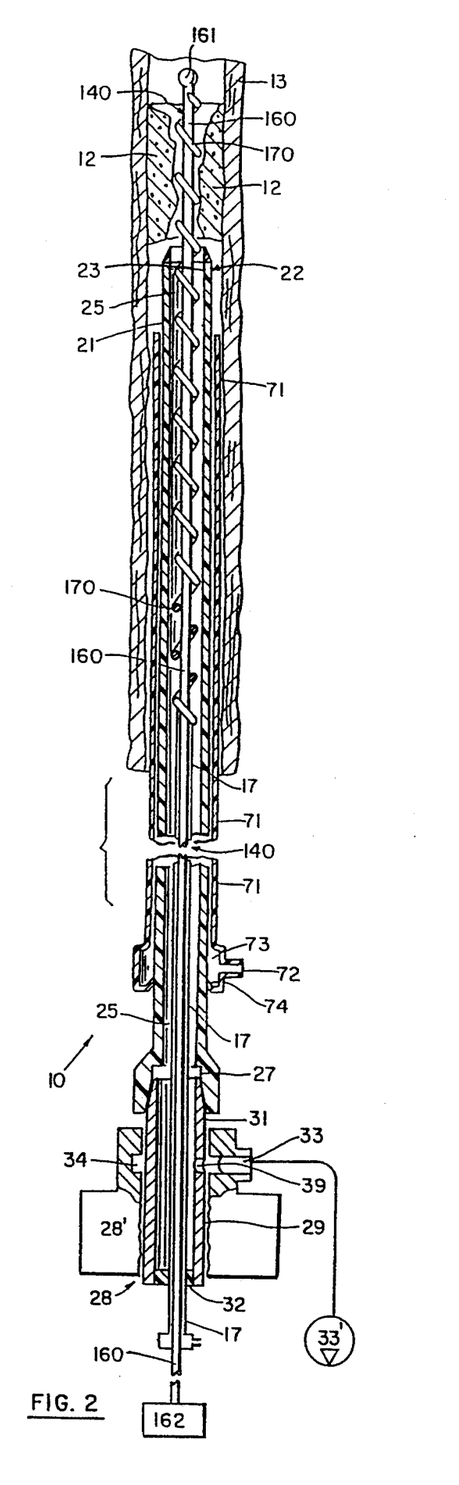
FIG. 2 shows a cross sectioned view of an atherectomy system with a flexible guide wire assembly having a flexible casing in the form of a helical wire wound around a flexible guide wire which incorporates an ultrasound probe. The middle portion of the atherectomy system is removed due to space limitations on the drawing sheet.

FIG. 2 shows the atherectomy system 10 (similar parts will be indicated by the same numbers throughout the FIGURES) for removing an obstruction 12 from within a patient's vessel, e.g., coronary artery 13. The atherectomy system comprises several elongated parts in a nested relationship, and their ends shall be referred to as "distal" meaning the end which goes into the vessel and "proximal" meaning the end portion which remains outside the vessel. Thus, "distal direction" or "distally" shall indicate a general direction from the proximal end to the distal end, and "proximal direction" or "proximally" shall refer to an opposite direction.

The atherectomy system comprises:

A flexible guide wire assembly 140 insertable into the vessel.

A flexible rotary catheter 21 slidable over the flexible guide wire assembly. The flexible rotary catheter has a tubular blade 22 at its distal end for separating and freeing an obstruction from the arterial wall and it defines a continuous passage 25 around the flexible guide wire assembly for ingesting the cut obstruction material (FIG. 5' shows an optional tubular blade design 22" which removes more of the obstruction material but also increases the probability of removing, or nicking, part of the vessel's wall, and is therefore considered a less preferred design option).

The flexible guide wire assembly is made of a thin walled steel extension tube 17 attached to a helical wire 170 which is shaped as an auger which is wound around and slidable and guided over flexible guide wire 160. A helical void is defined between the coils of the wire 170 for holding the obstruction material.

The flexible guide wire assembly's section which extends distally from the flexible rotary catheter into the artery provides a lever arm which aligns the flexible rotary catheter with the flexible guide wire assembly and the artery (note also FIG. 5).

When the flexible rotary catheter's distal end 23 bears against the arterial wall the contact force is spread on a relatively large area and the damage to the arterial wall is minimized.

Separating and freeing the sections of the obstruction from the vessel's wall uses less energy in comparison to other systems which pulverize the mass of the material of the obstruction. To illustrate this point, when a tubular blade cuts and extracts an obstruction with an outside diameter of 3 mm, an inside diameter (lumen) of 1 mm and a length of 10 mm the area that the tubular blade has to cut through is 94.25 square mm. If a pulverizing blade, for example as shown in U.S. Pat. No. 4,445,509 by Auth, is used to fragment the same obstruction to particles measuring 0.01 mm by 0.01 mm by 0.01 mm, the area that a pulverizing blade would have had to cut through is 37,699 square mm, and this area which is 400 times larger requires a much larger energy input to the blade, thereby substantially increasing the probability of traumatizing the artery.

Suction can be applied to the flexible rotary catheter through a port 33 which communicates with a groove 34 defined by the motor's housing, which communicates with hole 39, which communicates with the hollow shaft which communicates with proximal end of the continuous passage 25. Preferably the suction is provided by a positive displacement pump 33' such as a piston pump or a peristalic pump which tends to self regulate the evacuation process, limiting the amount of blood removed through the flexible rotary catheter to the volume that is positively displaced by the pump. When only free flowing blood is present in the continuous passage, the negative pressure in the continuous passage drops. As obstruction material enters the continuous passage the negative pressure rises and pulls the cut material proximally (the level of negative pressure can be limited by an internal relief valve in the pump). The suction can be synchronized with the rotation of the tubular blade, or it can be otherwise selectively controlled to further minimize blood evacuation. The suction cooperates with mechanical agitation and conveyance taking place in the continuous passage in moving the obstruction material proximally in the flexible rotary catheter.

Coupling means at the proximal end of the flexible rotary catheter in the form of a conical seat 27 couples it to drive means in the form of a motor having a housing 28 and a hollow shaft 29 with a matching tapered end 31 and a seal 32 at its other end. The hollow shaft and seal are slidingly disposed around the proximal end of the flexible guide wire assembly.

The guide wire 160 contains means for transmission of energy between an ultrasound transducer 161 mounted at its distal end and a base unit 162 connected to its proximal end. The base unit sends, through the guide wire, electrical energy to the transducer and receives back a signal which is translated by the base unit to a map of the surrounding obstruction and tissue. Relying on this information the physician can push the guide wire forward without risking inadvertent perforation of the arterial wall.

The flexible guide wire assembly 140 does several things: It act as a barrier which prevents the obstruction material's distal movement during the atherectomy. It also restrains the freed obstruction sections from freely rotating around the flexible guide wire assembly, and to the extent that they do rotate, this rotation is used to urge the freed obstruction sections proximally in the continuous passage. In addition, when the flexible guide wire assembly has to be inserted into a tight obstruction, the helical wire can be threaded into the obstruction by rotating it, causing the helical wire to pull itself into and across the obstruction. Further, the helical wire guides the flexible rotary catheter 170, taking up the free play between the guide wire 160 and the flexible rotary catheter.

Figures 6, 7, 8, 9, 10, 11, 12, 13:
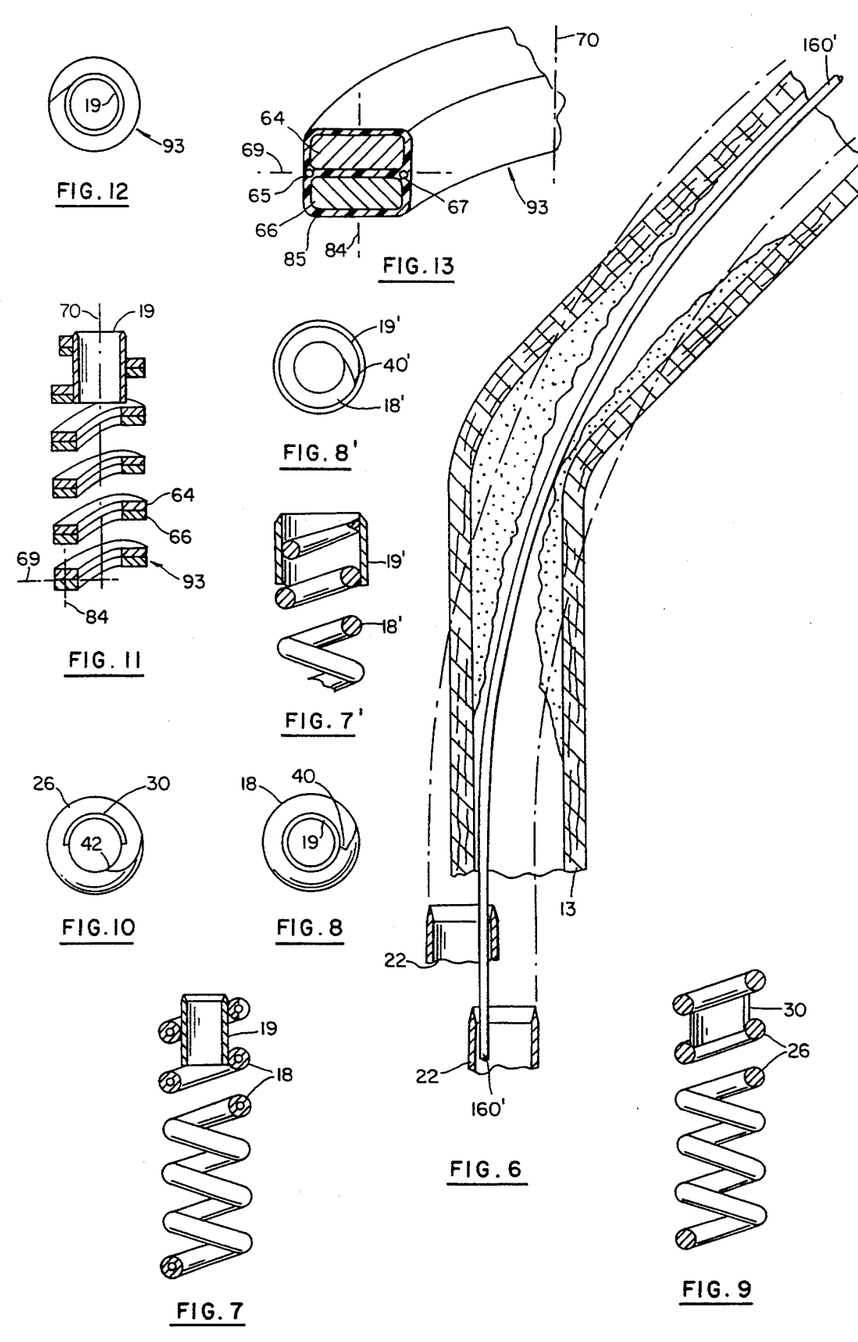
FIG. 6 shows, using intermittent lines, the possible boundaries of possible trajectories of the system in a cross sectioned, curved obstructed artery, when the atherectomy process is done over a flexible guide wire without the benefit of the additional accurate guidance provided by the casing. This illustrates one of the advantages of using the flexible casing.
FIG. 7 shows an enlarged, partially sectioned view of the distal end section of a helical wire where the distal entry to the void, which is defined between the coils, is selectively closed by a thin walled cylinder. The helical wire is made of a tube through which non-mechanical energy can be conveyed to the distal end to preferably assist in screwing the helical wire through an obstruction, in addition to mechanical energy that can be transmitted through the helical wire itself.
FIG. 8 shows the end view of the helical wire shown in FIG. 7.
FIG. 9 shows an enlarged, partially sectioned view of the distal end section of a helical wire where the distal entry to the helical void, which is defined between the coils, is selectively closed by a thin walled cylindrical section.
FIG. 10 shows the end view of the helical wire shown in FIG. 9.
FIG. 11 shows an enlarged, sectioned view of the distal end section of a helical wire made of two flat layers, where the distal entry to the helical void which is defined between the coils is selectively closed by a thin walled cylinder.
FIG. 12 shows the end view of the helical wire shown in FIG. 11.
FIG. 13 shows a further enlargement of the cross section of the helical wire of FIG. 11.

FIG. 5 is used to illustrate how the flexible casing, in the form of the helical wire 170, accurately guides the flexible rotary catheter 21 and the tubular blade to separate the obstruction from the vessel's wall without injuring it. For comparison, FIG. 6 shows the wider range of trajectories of the system, where a flexible guide wire without a casing is used. Thus, FIG. 6 illustrates the advantage of the accurate guidance that is provided by adding the flexible casing, which among other things, reduces the probability of injuring the vessel's wall.

Referring back to FIG. 2, a flexible sleeve 71 in which the flexible rotary catheter is disposed protects the arterial wall from the rotating catheter, and can be used to introduce the flexible rotary catheter into the vessel. Means for introducing fluids into the vessel are connected to the flexible sleeve in the form of a nipple 72 leading into an annular chamber 73 which communicates with the sleeve. The annular chamber is equipped with a seal 74 which seals around the flexible rotary catheter and forces fluid entering the nipple 72 to move distally in the sleeve around the flexible rotary catheter.

FIG. 3 shows a second embodiment of an ultrasound probe 163 having protrusions 164 on its distal end and a smooth proximat mid-section 165 for transmitting and receiving ultrasound energy. The protrusions allow a physician to use the probe as a drill by rotating the guide wire, and thereby enabling it to cross very tight or total obstructions with the relative safety of knowing the probe's position relative to arterial wall, via the base unit such as the base unit 162 in FIG. 2. Alternate non-mechanical energy, for example heat, laser energy or other frequencies of electromagnetic waves, could be used with proper modification of the guide wire 160 to carry such frequencies, and of the probe and base unit to transmit and receive such frequencies. Such energy being sent from the base unit to the probe could also be used to assist the probe in penetrating through the obstruction, with or without rotation thereof. Optionally, very small protrusions can be attached to the probe, e.g., diamond particles, to enable the probe, when it is rotated, to drill through the obstruction.

The ultrasound energy which is emitted by the probe is partially transmitted to the helical wire 170 and to the adjacent obstruction material to assist the helical wire 170 in threading itself through the obstruction material.

FIG. 4 shows a distal portion of a flexible guide wire 160 disposed in a deflecting sleeve 82' for deflecting the trajectory of the flexible guide wire in the vessel. The deflecting sleeve 82' is a scaled down version of the deflecting sleeve shown in FIGS. 20 and 21 and performs in the same manner. The deflecting sleeve can be used to guide the whole flexible guide wire assembly through the vessel.

FIG. 7 shows an enlarged, partially sectioned view of the distal end section of a casing in the form of a helical wire 18 where the distal entry to the void which is defined between the coils is selectively closed by a thin gate in the form of a thin walled cylinder 19 attached to and located inside the casing (the term "selectively closed" means that the gate prevents the guide wire from entering the void, but it minimally interferes with the entry of obstruction material into the void). The helical wire is made of a tube through which non-mechanical energy, for example laser energy, can be conveyed to the distal end to assist in threading the helical wire through an obstruction in addition to the mechanical energy that can be transmitted through the tube itself.

FIG. 8 shows the end view of the helical wire shown in FIG. 7, having a sharp end tip 40.

FIG. 7' shows an enlarged, partially sectioned view of the distal end section of a casing in the form of a helical wire 18', where the distal entry to the void which is defined between the coils is selectively closed by a thin gate in the form of a thin walled cylinder 19' attached to and located outside of the casing.

FIG. 8' shows the end view of the helical wire shown in FIG. 7' having a helical wire 18' with a sharpened tip 40'.

FIG. 9 shows an enlarged, partially sectioned view of the distal end section of a casing in the form of a helical wire 26 where the distal entry to the helical void defined between the coils is selectively closed by a gate in the form of a thin walled cylindrical section 30 which is attached to and is located inside the casing.

FIG. 10 shows the end view of the helical wire shown in FIG. 9, having a sharpened tip 42.

FIGS. 11 and 12 shows an enlarged, sectioned view of the distal end section of a helical wire made of two flat layers, where the distal entry to the helical void defined between the coils is selectively closed by a thin walled cylinder which is attached to and is located inside the casing.

FIG. 11 shows an enlarged, sectioned view of the distal end section of a helical wire 93 made of two flat layers 64 and 66, where the distal entry to the helical void defined between the coils is selectively closed by a thin walled cylinder 19. By forming the helical wire 93 from two layers, the cross section modulus of the helical wire 93 around an axis 69, which is perpendicular to the helical wire's axis 84, is decreased (for orientation, axis 84 is parallel to the casing axis 70).

FIG. 12 shows the end view of the helical wire shown in FIG. 11.

FIG. 13 shows a further enlargement of the cross section of the helical wire of FIG. 12. The layers 64 and 66 are encapsulated in a plastic material 85 which holds them together and makes them thread through the obstruction material in unison, as one piece, but is sufficiently flexible to allow their cross section modulus to be that of two separate layers. Non-mechanical energy conduits 65 and 67, for example electrical wires or fiber optical bundles, are also encapsulated by the plastic material. Preferably, the plastic material has a slippery outer surface to ease its insertion through the vessel and its threading through the obstruction material.

Figure 16:
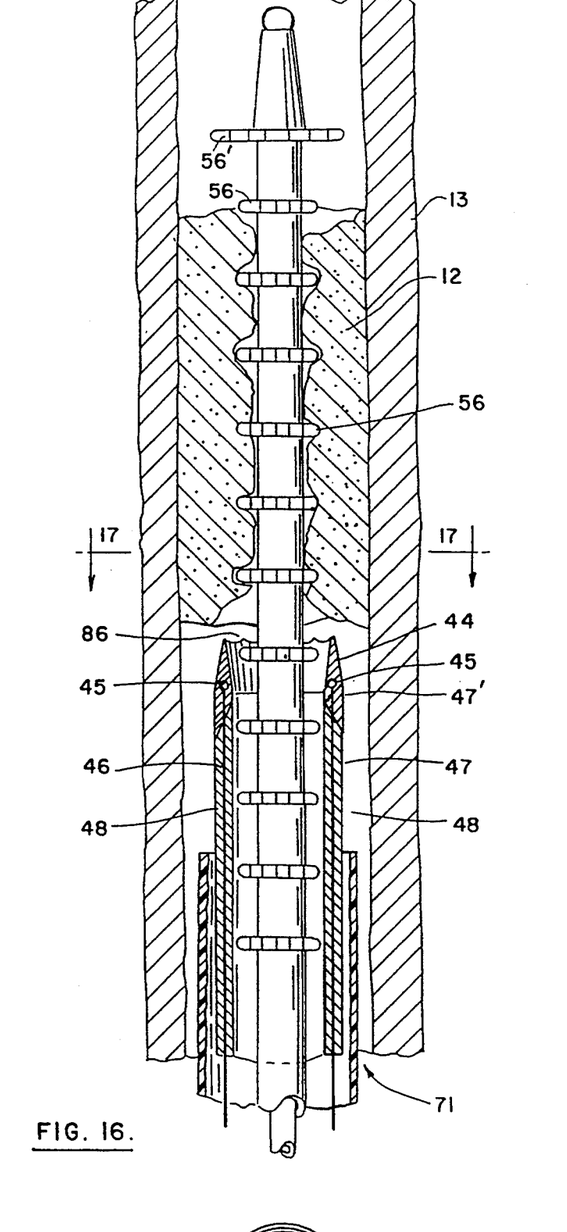
FIG. 16 shows a cross sectioned view of the distal end portion of an atherectomy system with a tubular-blade, which utilizes auxiliary non-mechanical energy, disposed over a flexible guide wire assembly having barrier means in their expanded position.

FIG. 16 shows a distal end portion of an atherectomy system having a tubular blade 44 with teeth 86 and a ring shaped heating element 45 built into the blade, to which non-mechanical energy is brought by means of two flexible conduits 46 and 47 carried in a wall of a flexible rotary catheter 48. The heating can be done electrically, in which case the conduits 46 and 47 are electrical wires and the heating element can be a resistive element, or the heating can be done with laser energy in which case the conduits 46 and 47 can be optical fibers and the heating element can serve to absorb the laser energy from the distal end of the optical fibers and translates it to heat and distributing it to the tubular blade 44. Optionally, the tubular blade can be made from semi-transparent or transparent material, and part or all of the laser energy can be transmitted, respectively, to the obstruction material.

A flexible guide wire assembly has barriers 56 to counter distal movement of surrounding obstruction material. The barriers can be made of thin plastic jacket 88 with series of slits. In their open position the elements form a barrier 56 to prevent the obstruction material from moving distally in the vessel and in the continuous passage while the flexible rotary catheter cuts and ingests the obstruction material. The diameter of the stretched out arms of the top barrier element 56' can be made larger than the inner diameter of the flexible rotary catheter to block a larger cross sectional area of the artery whereas the diameter of the stretched arms of the other barrier elements are made to fit inside the flexible rotary catheter which they guide and slidably support.

Since that obstruction material is positively held in voids defined between elements 56 and since the non-mechanical energy delivered to the tubular blade through conduits 46 and 47 eases the coring process, it may be possible to cut softer obstruction material by pushing the catheter without rotating it, especially where there is an anatomical reason not to impart torque onto the vessel. However, rotating the catheter and blade provides more effective cutting and also reduces the linear frictional drag between the catheter and the vessel, and is, therefore, preferable in most cases.

Figure 14:
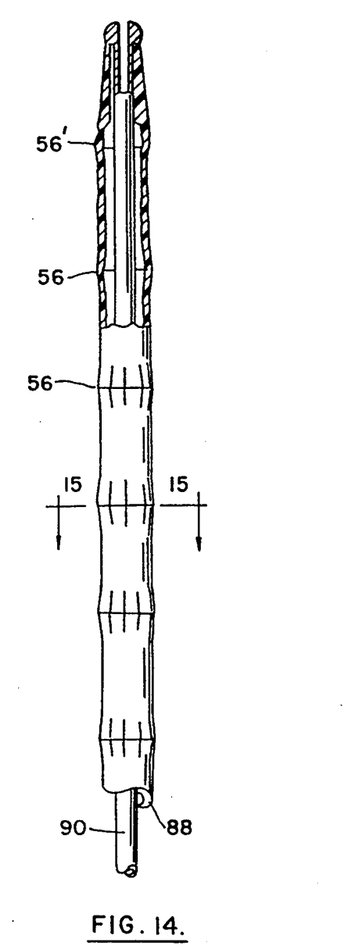
FIG. 14 shows the flexible guide wire assembly shown in FIG. 16 with the barrier means in their closed position.
Figure 15:
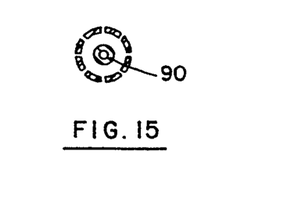
FIG. 15 shows a cross sectioned view of the system shown in FIG. 14 along a line 15—15 marked on FIG. 14.

FIG. 15 shows a cross sectioned view of the system shown in FIG. 14 along a line 15—15 marked on FIG. 14.

FIG. 14 shows the flexible guide wire assembly shown in FIG. 16 with the barrier means 56 in their closed position. The barrier means can be selectively expanded by holding the proximal end of a wire 90 while pushing the jacket 88 forward until jacket sections 56 fold.

Figure 17:
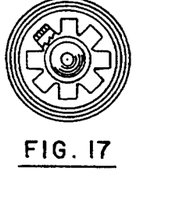
FIG. 17 shows a cross sectioned view of the atherectomy system assembly shown in FIG. 16 along a line 17—17 marked on FIG. 16.

FIG. 17 shows a cross sectioned view of the flexible guide wire shown in FIG. 16 along a line 17—17 marked on FIG. 16.

Figure 18:
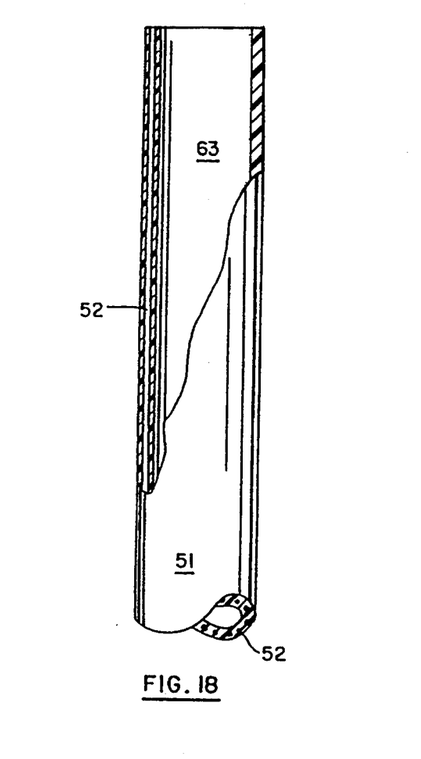
FIG. 18 shows a cross sectioned view of an atherectomy system where a radiation emission is used to separate the obstruction from the vessel's wall.

FIGS. 18 show an atherectomy system having a flexible catheter 51 where separation of the obstruction from the vessel is done with a radiation emitting device through optical fibers 52 which emits laser energy through their distal ends. The radiation energy cuts the obstruction by cutting a narrow channel in it and the continuous passage 63 ingests the cut obstruction material as in previous embodiments. Similarly to the tubular-blade, the embodiment of FIG. 18 separates the obstruction from the vessel's wall and uses less energy in comparison to other laser based systems which pulverize the bulk of the material of the obstruction. Using the same hypothetical obstruction which was used in the previous numerical example (having an outside diameter of 3 mm, an inside diameter of 1 mm and a length of 10 mm) with the system shown in FIG. 18, when radiation energy is used to make a 0.1 mm wide peripheral cut, it has to disintegrate 9.11 cubic mm of material which is 14.5% of the obstruction's volume. The flexible catheter 51 can be rotatably disposed in any of the sleeves shown in connection to the embodiments of the present invention. By using a sleeve equipped with a toroidal chamber to block blood flow as explained above and by introducing fluid, saline solution for example, through the sleeve or the flexible catheter, a working medium of choice can be created to suit a specific type of radiation and to allow visual or spectroscopic analysis of the vessel's lumen.

When a plurality of optical fibers 52 are used, as shown in FIG. 18, it may be possible to cut and separate the obstruction from the vessel's wall by pushing the catheter 51 distally while slightly rotating it back and forth, to minimize the frictional torque imparted on the vessel's wall.

Figure 19:
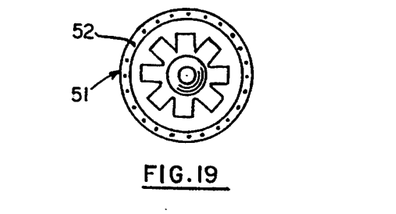
FIG. 19 shows the end view of the system shown in FIG. 18 with the flexible guide wire assembly having barrier means in their expanded position, similar to the guide wire assembly shown in FIG. 17.

FIG. 19 shows a distal end view of the system shown in FIG. 18 with the guide wire assembly that has been incorporated in the embodiment of FIG. 16.

Figure 20:
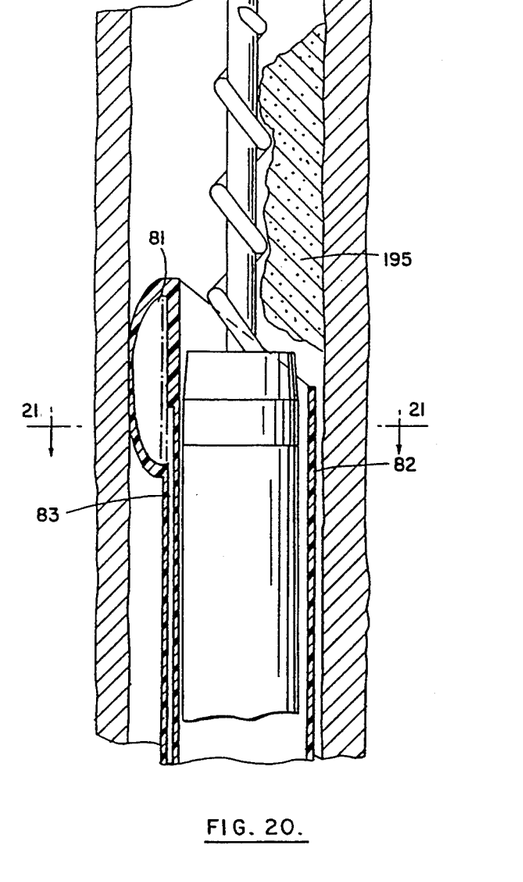
FIG. 20 shows a cross sectioned view of an atherectomy system with an inflatable chamber located at the distal end of the flexible sleeve in which a flexible rotary catheter is slidably and rotatably disposed.
Figure 21:
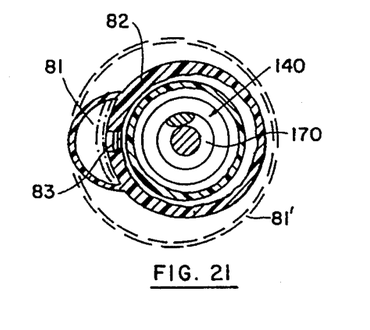
FIG. 21 shows a cross sectioned view of the system shown in FIG. 20 along a line 21—21 marked on FIG. 20.

FIGS. 20 and 21 show a biasing means in the form of an asymmetrical inflatable chambers 81 formed at the distal end of a flexible deflecting sleeve 82 which, when inflated through a channel 83 formed in the sleeve's wall, bears against the vessel's wall, as shown in solid lines, eccentrically biasing the flexible sleeve and the coring means. When deflated, as shown by phantom lines, the chamber conforms to the sleeve to minimize interference with its insertion into the vessel. Alternatively the chamber can be shaped as an asymmetrical toroidal inflatable chamber 81' as shown in FIG. 21 by interrupted lines. This chamber, when inflated, establishes a peripheral contact with the vessel's wall and thereby blocks blood flow between the sleeve and the arterial wall, as well as eccentricaly biasing the sleeve (it can be understood that a symmetrical toroidal chamber can be provided for the purpose of blocking the flow around the sleeve without eccentrically biasing the sleeve). Any of the above mentioned chambers can also be inserted into the lumen that has been cut by the tubular blade, to be inflated therein and to further widen the lumen, however, such a procedure may have some of the drawbacks of angioplasty.

Figure 22:
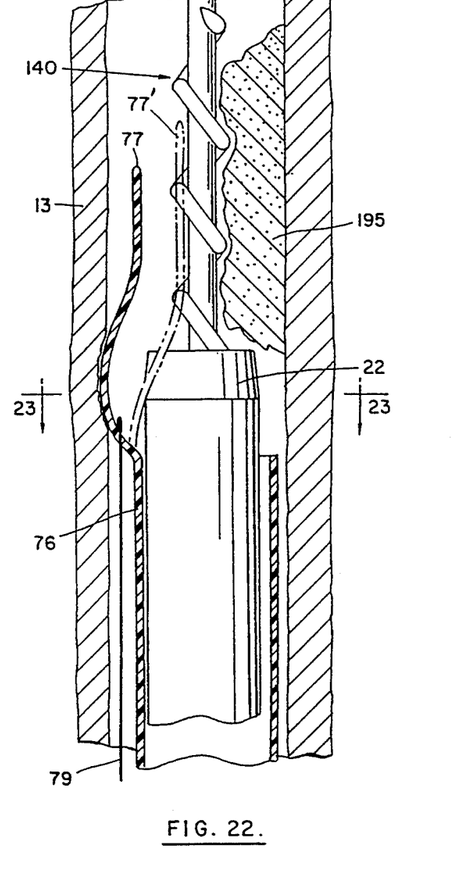
FIG. 22 shows a cross sectioned view of an atherectomy system with a flexible sleeve having a selectively actuable tongue at its distal end.
Figure 23:
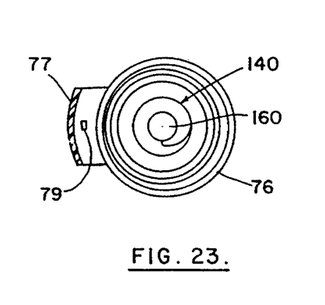
FIG. 23 shows a cross sectioned view of the tongue shown in FIG. 22 along the line 23—23 marked on FIG. 22.

FIGS. 22 and 23 show an atherectomy system where a flexible sleeve 76 has a tongue 77 which can be used when coring an eccentric obstruction 195. In such a case the tongue can be inserted opposite of the obstruction to protect an arterial wall 78 and bias the trajectory of the coring means into the obstruction. The tongue can be energized against the arterial wall by tensioning a flexible rope 79, moving the tongue from its relaxed position shown in a phantom line in FIG. 22 and marked 77' to the position shown in solid lines and marked 77 (which may ease the insertion of the sleeve 76).

Figure 24:
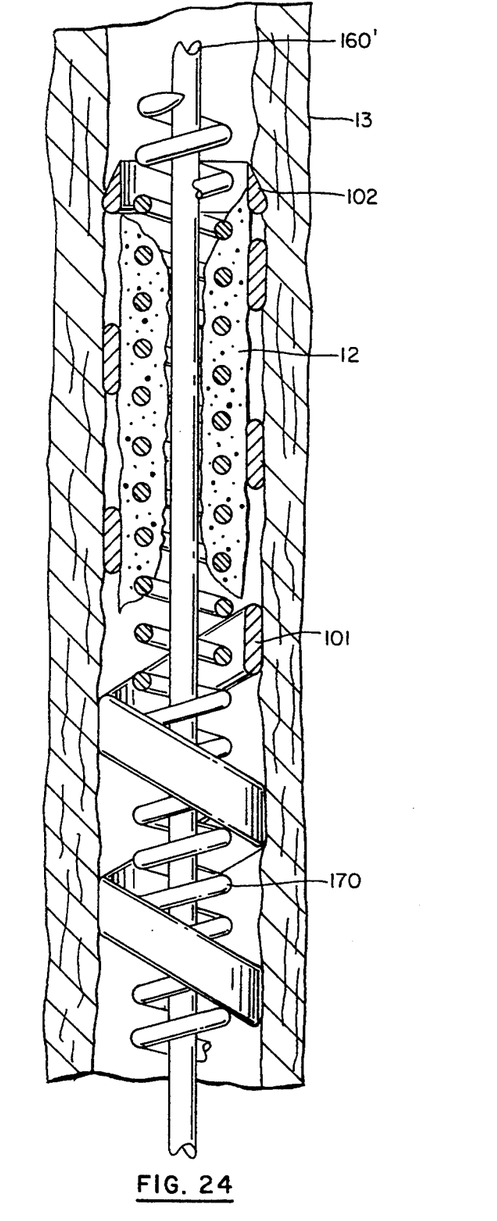
FIG. 24 shows a cross sectioned view of a distal portion of an atherectomy system with a flexible guide wire assembly having a flexible casing in the form of a helical wire wound around a flexible guide wire, and a flexible rotary catheter in the form of an open coil flat wire spring.

FIG. 24 shows a cross sectioned view of a distal portion of an atherectomy system with a flexible guide wire assembly having a flexible casing in the form of a helical wire 170 wound around a regular flexible guide wire 160', and a flexible rotary catheter in the form of an open coil flat wire spring 101 which is attached, at its distal end, to a tubular blade 102.

Figure 25:
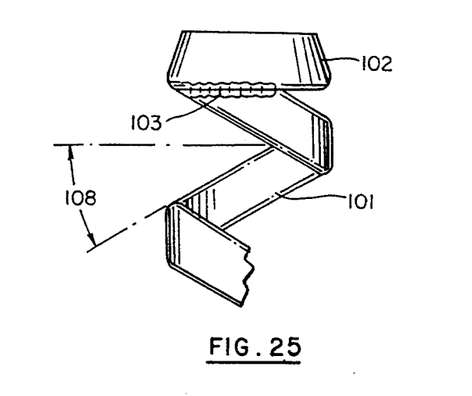
FIG. 25 shows a distal portion of the open coil flat wire spring flexible rotary catheter shown in FIG. 24.

FIG. 25 shows a distal portion of the flexible rotary catheter which is shown in FIG. 24, and the tubular blade 102 which is attached to the spring 101 by a weldment 103. Numeral 108 designates the helix angle of the spring 101. When the angle 108 is decreased the stiffness of the spring 101 is decreased and vise versa.

Figure 26:
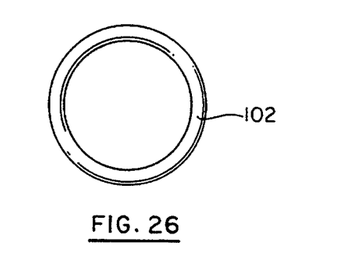
FIG. 26 shows the end view of the helical wire shown in FIG. 25.

FIG. 26 shows the end view of the tubular blade.

Figure 27:
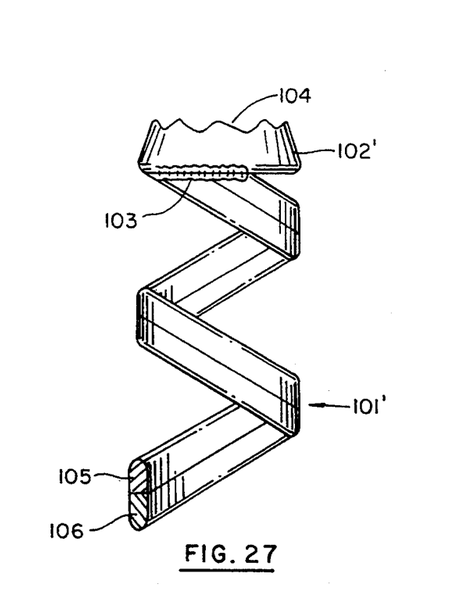
FIG. 27 shows a modified distal portion of the open coil flat wire spring flexible rotary catheter shown in FIG. 24 where teeth are formed on the tubular cutting edge of the blade and the flat wire spring is constructed of two separate halves, to make it softer and easier to bend in order to follow the vessel's curves without substantially reducing its torque carrying capabilities.

FIG. 27 shows a modified distal portion of the open coil flat wire spring flexible rotary catheter shown in FIG. 24 and 25, where teeth 104 are formed on the cutting edge of the tubular blade 102' and the flat wire spring 101' is constructed of two separate halves 105 and 106, to make it softer and easier for the spring 101' to bend and follow the vessel's curves, but without substantially reducing its torque carrying capabilities.

The atherectomy system can be manufactured in different diameters and lengths depending on the size and site of artery that it is intended for and on whether the system is to be used percutaneously (which means gaining access to the artery through the skin) or intra-operatively (that is when the vessel is surgically exposed for inserting the system into it).

It can be noted from the FIGURES that the basic components of the atherectomy system can accept several optional features: The flexible rotary catheter can be made from plastic or metal. The coring means can vary. A regular guide wire can be used or a guide wire assembly having incorporating a helical wire or radial barrier means can be used. The sleeve can be equipped with mechanical or hydraulic biasing and flow blocking means.

By combining a certain flexible rotary catheter with a certain guide wire assembly (or with a flexible guide wire) and optionally adding a sleeve with or without biasing means, the characteristics of the system can be customized to treat individual patients. This is beneficial since the characteristics of atherosclerotic obstructions vary widely in their length, cross-sectional geometry and hardness, and in their location within the body.

OPERATION

The process for removing an obstruction from within a vessel comprises the following steps:

Inserting into the vessel, into the obstruction, a flexible guide wire.

Separating the obstruction from an inner wall of the vessel with a tubular blade which is advanced over and guided by the flexible guide wire.

Removing the flexible guide wire together with the separated obstruction out of the vessel.

The process can be modified as follows:

Inserting into the vessel, into the obstruction, a flexible guide wire, and then, inserting into the obstruction, over the a flexible guide wire, a flexible casing.

Separating the obstruction from an inner wall of said vessel with a tubular blade which is advanced over and guided by the casing.

Removing the casing with the separated obstruction out of the vessel.

Suction, which is preferably provided by a positive displacement pump means, may be used to assist the mechanical action in enabling the cut obstruction material to move proximally in the continuous passage.

The sequence of insertion of the components into the artery may vary depending on the nature and the location of the obstruction and the preferences of the medical staff. Additional steps may be added to assist the process. A standard guiding catheter, which is either straight or pre-formed, may function as a sleeve and be inserted into the vessel to assist in placing the flexible guide wire assembly and the atherectomy catheter in the obstruction site.

While the present invention has been illustrated by a limited number of embodiments, it should be understood that various modifications and substitutions may be made without departing from the spirit of the invention or the scope of the claims.

I claim:

1. A system for removing an obstruction, in sections, from within a vessel of a body, comprising in combination:

a flexible guide wire insertable into the vessel, a flexible rotary catheter slidable over the flexible guide wire and having a tubular blade at its distal end for separating the obstruction from a wall of the vessel, the tubular blade being affixed to the flexible rotary catheter for rotating together with it, a passage, defined around the flexible guide wire by the flexible rotary catheter for accepting sections of the obstruction which was separated from the wall of the vessel.

2. A system as in claim 1, the flexible rotary catheter is slidably disposed in a flexible sleeve.

3. A system as in claim 2, the flexible sleeve having a biasing means on its side for eccentrically biasing the flexible sleeve in the vessel.

4. A system as in claim 3, the biasing means comprising an inflatable chamber.

5. A system as in claim 3, the biasing means comprising a tongue at the distal end of the flexible sleeve for eccentrically biasing the flexible sleeve in the vessel.

6. A system for removing an obstruction, in sections, from within a vessel of a body, comprising in combination:

a flexible guide wire assembly insertable into the vessel, a flexible rotary catheter slidable over the flexible guide wire assembly and having a tubular blade at its distal end for separating the obstruction from a wall of the vessel, the tubular blade being affixed to the flexible rotary catheter for rotating together with it, a passage, defined around the flexible guide wire assembly by the flexible rotary catheter for accepting sections of the obstruction which was separated from the wall of the vessel.

7. A system as in claim 6, wherein the flexible guide wire assembly comprises a flexible guide wire surrounded by a flexible casing.

8. A system as in claim 7, wherein the flexible guide wire is slidable relative to the flexible casing.

9. A system as in claim 7, wherein the flexible casing comprises a helical wire.

10. An system as in claim 6, wherein the flexible rotary catheter is slidably disposed in a flexible sleeve.

11. A system as in claim 10, wherein the flexible sleeve having a biasing means on its side for eccentrically biasing the flexible sleeve in the vessel.

12. A system as in claim 11, wherein the biasing means comprises an inflatable chamber.

13. A system as in claim 11, the biasing means comprising a tongue at the distal end of the flexible sleeve for eccentrically biasing the flexible sleeve in the vessel.

14. A process for removing an obstruction from within a vessel comprising the following steps:

inserting a flexible guide wire into the vessel and into the obstruction, inserting a catheter annularly over the flexible guide wire and into the vessel, wherein the catheter has a tubular blade at its distal end, advancing the catheter and the tubular blade over the obstruction and the flexible guide wire, thereby separating the obstruction from a wall of the vessel and ingesting it into the catheter through the tubular blade and, removing the separated obstruction from the vessel.

15. A process for removing an obstruction from within a vessel comprising the following steps:

inserting a flexible guide wire into a vessel and into an obstruction, inserting a flexible casing, over the flexible guide wire, and into the obstruction, inserting a catheter annularly over the flexible casing and into the vessel, wherein the catheter has a tubular blade at its distal end, and, advancing the catheter and tubular blade over the obstruction and the flexible casing, thereby separating the obstruction form a wall of the vessel and ingesting it into the catheter through the tubular blade, and, removing the separated obstruction from the vessel.

* * * * *